United States Patent
Kravtchenko et al.

(10) Patent No.: US 7,862,803 B2
(45) Date of Patent: *Jan. 4, 2011

(54) OXIDIZING COMPOSITION FOR TREATING KERATIN MATERIALS BASED ON AMPHIPHILIC POLYMERS OF AT LEAST ONE ETHYLENICALLY UNSATURATED MONOMER WITH A SULPHONIC GROUP AND COMPRISING A HYDROPHOBIC PORTION

(75) Inventors: Sylvain Kravtchenko, Asnieres (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 1241 days.

This patent is subject to a terminal disclaimer.

(21) Appl. No.: 10/451,409

(22) PCT Filed: Dec. 19, 2001

(86) PCT No.: PCT/FR01/04077

§ 371 (c)(1),
(2), (4) Date: Dec. 1, 2003

(87) PCT Pub. No.: WO02/051369

PCT Pub. Date: Jul. 4, 2002

(65) Prior Publication Data

US 2004/0074015 A1    Apr. 22, 2004

(30) Foreign Application Priority Data

Dec. 22, 2000  (FR) .................................. 00 16954
Jan. 11, 2001  (FR) .................................. 01 00328

(51) Int. Cl.
*A61Q 5/08* (2006.01)
*A61Q 5/04* (2006.01)
*A61Q 5/00* (2006.01)

(52) U.S. Cl. ..................... 424/62; 424/70.2; 424/70.11; 424/401

(58) Field of Classification Search ....................... None
See application file for complete search history.

(56) References Cited

U.S. PATENT DOCUMENTS

| 5,143,518 A | * | 9/1992 | Madrange et al. ............... 8/405 |
| 5,609,862 A | | 3/1997 | Chen et al. |
| 6,110,451 A | | 8/2000 | Matz et al. |
| 6,149,900 A | | 11/2000 | Afriat et al. |
| 6,180,118 B1 | | 1/2001 | Maubru |
| 6,645,476 B1 | * | 11/2003 | Morschhauser et al. .... 424/70.1 |
| 7,338,534 B2 | * | 3/2008 | Kravtchenko et al. .......... 8/405 |

FOREIGN PATENT DOCUMENTS

| EP | 0 750 899 | 1/1997 |
| FR | 2 753 372 | 3/1998 |
| JP | 5-246828 | 9/1993 |
| JP | 6-107526 | 4/1994 |
| JP | 10-101532 | 4/1998 |
| JP | 11-180824 | 7/1999 |
| WO | WO 00/37041 | 6/2000 |

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

The invention concerns a cosmetic composition for treating keratinous materials comprising in a carrier suitable for keratinous materials: (a) at least an amphiphilic polymer comprising at least an ethylenically unsaturated monomer with sulphonic group, in free form or partly or completely neutralized and further at least a hydrophobic part; (b) at least an oxidizing agent.

41 Claims, No Drawings

OXIDIZING COMPOSITION FOR TREATING KERATIN MATERIALS BASED ON AMPHIPHILIC POLYMERS OF AT LEAST ONE ETHYLENICALLY UNSATURATED MONOMER WITH A SULPHONIC GROUP AND COMPRISING A HYDROPHOBIC PORTION

The present invention relates to a gelled oxidizing composition for treating keratin materials, comprising an amphiphilic polymer comprising at least one ethylenically unsaturated monomer containing a sulfonic group, in free form or partially or totally neutralized form, and also at least one hydrophobic portion, and also to its uses for dyeing, permanently reshaping or bleaching human keratin fibers and in particular the hair.

It is known practice to bleach keratin fibers, and in particular human hair, with bleaching compositions containing one or more oxidizing agents. Among the oxidizing agents conventionally used that may be mentioned are hydrogen peroxide or compounds capable of producing hydrogen peroxide by hydrolysis, such as urea peroxide or persalts, for instance perborates, percarbonates and persulfates, hydrogen peroxide and persulfates being particularly preferred.

Said bleaching compositions are mainly in the form of anhydrous products (powders or creams) containing alkaline compounds (amines and alkaline silicates) and a peroxygenated reagent such as alkali metal or ammonium persulfates, perborates or percarbonates, which is diluted at the time of use with an aqueous hydrogen peroxide composition.

Bleaching compositions may also result from the mixing, at the time of use, of the anhydrous powder of peroxygenated reagent with an aqueous composition containing the alkaline compounds and another aqueous composition containing hydrogen peroxide.

Bleaching compositions are also in the form of ready-to-use thickened aqueous hydrogen peroxide compositions.

For the purposes of the invention, the expression "ready-to-use composition" means the composition intended to be applied, without modification, to the keratin fibers, i.e. it may be stored without modification before use or may result from the extemporaneous mixing of two or more compositions.

It is moreover known practice to dye keratin fibers, and in particular human hair, with dye compositions containing oxidation dye precursors, in particular ortho- or para-phenylenediamines, ortho- or para-aminophenols, and heterocyclic compounds, which are generally known as oxidation bases. Oxidation dye precursors, or oxidation bases, are colorless or weakly colored compounds which, when combined with oxidizing products, can produce colored compounds and dyes by a process of oxidative condensation. It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The oxidizing agent present in the oxidizing composition as defined above may be chosen from the oxidizing agents conventionally used for the oxidation dyeing of keratin fibers, and among which mention may be made of hydrogen peroxide or compounds capable of producing hydrogen peroxide by hydrolysis, such as urea peroxide or persalts, for instance perborates and persulfates. Hydrogen peroxide is particularly preferred.

To localize the bleaching or dye product being applied to the hair so that it does not run onto the face or outside the areas that it is intended to bleach, use has been made hitherto of conventional thickeners such as crosslinked polyacrylic acid, hydroxyethylcelluloses, certain polyurethanes and waxes, and also, in the case of aqueous bleaching compositions, of mixtures of nonionic surfactants with an HLB (Hydrophilic-Lipophilic Balance) value, which, when suitably selected, generate the gelling effect when they are diluted with water and/or surfactants.

However, the Applicant has found that the thickening systems mentioned above do not produce bleaching results that are sufficiently powerful and homogeneous, and leave the hair coarse.

Moreover, it has also been found that ready-to-use bleaching compositions containing the oxidizing agent(s) and also the thickening systems of the prior art do not allow a sufficiently precise application without the composition running or without reductions in viscosity over time.

It is also known that the technique most commonly used for permanently reshaping the hair consists, in a first stage, in opening the —S—S-disulfide bonds of keratin (cystine) with a composition containing a suitable reducing agent (reduction step) and then, after the hair thus treated has been rinsed, in reconstituting said disulfide bonds in a second stage by applying to the hair, which has been placed under tension beforehand (curlers and the like), an oxidizing composition (oxidation step, also known as the fixing step) so as finally to give the hair the desired shape. This technique thus makes it possible either to make the hair wavy or to relax it or straighten it out. The new shape given to the hair by means of a chemical treatment as above is remarkably long-lasting and especially withstands the action of washing with water or shampooing, unlike the conventional simple techniques of temporary reshaping, such as hairsetting.

The reducing compositions that may be used to carry out the first step of a permanent-waving operation generally contain sulfites, bisulfites, alkylphosphines or, preferably, thiols, as reducing agents. Among the latter, reducing agents that are conventionally used are cysteine and its various derivatives, cysteamine and its derivatives, thiolactic acid or thioglycolic acid, the salts thereof and the esters thereof, especially glyceryl thioglycolate.

As regards the oxidizing compositions required to carry out the fixing step, use is usually made, in practice, of compositions based on aqueous hydrogen peroxide solution.

Moreover, cosmetic formulations in the form of transparent gels have been sought for many years. This type of presentation is very much appreciated by consumers for esthetic reasons and for reasons of ease and comfort of use.

The gel form usually presents formulators with practical concerns: ease with which the product can be taken from its packaging without significant loss, limiting of the diffusion of the product to the local area of treatment, and ability to use amounts that are sufficient to obtain the desired cosmetic effect. This objective is important for oxidizing formulations used in hair dyeing, and for permanent-waving or bleaching of the hair. These formulations must spread well and be distributed uniformly along the keratin fibers, and must not run onto the forehead, the nape of the neck or the face, or into the eyes.

It is generally difficult to obtain gels based on peroxide such as hydrogen peroxide, which are stable on storage, by using conventional water-soluble gelling agents and/or thickeners, for example those of the crosslinked acrylic polymer type, for instance those sold under the name Carbopol® by the company Goodrich. Peroxides are used in cosmetics in the form of aqueous acidic solutions for reasons of stability. In the presence of conventional gelling agents, they usually lead to substantial variations in the viscosity of the gel during storage.

Gels based on hydrogen peroxide containing a gelling agent formed by reacting a quaternized hydroxyethylcellulose such as Celquat® (product sold by National Starch), an aqueous solution at 15% by weight of a noncrosslinked poly (2-acrylamido-2-methylpropanesulfonic acid) polymer such as Cosmedia HSP-1180® (product sold by Henkel) and a sodium polystyrene sulfonate such as Flexan 3® (product sold by National Starch), used in particular concentrations, are known in U.S. Pat. No. 4,804,705.

The Applicant has discovered, surprisingly, that it is possible to obtain ready-to-use bleaching compositions that do not run, and thus remain correctly localized at the point of application, and that also make it possible to obtain powerful and homogeneous bleaching results while at the same time leaving the hair less coarse, if an effective amount of a particular amphiphilic polymer is introduced into the composition.

The Applicant has also discovered, surprisingly, a novel family of thickeners and/or gelling agents for obtaining transparent gels based on oxidizing agents and preferably hydrogen peroxide or an oxidizing compound capable of releasing hydrogen peroxide, which are stable on storage. These agents are amphiphilic polymers comprising at least one ethylenically unsaturated monomer containing a sulfonic group, in free form or partially or totally neutralized form, and also at least one hydrophobic portion. These novel gelling agents do not affect the oxidizing properties of the hydrogen peroxide or of a compound capable of producing hydrogen peroxide by hydrolysis, which is present in the gel thus formed.

One subject of the present invention is thus a cosmetic and/or dermatological composition for treating keratin materials, comprising, in a support that is suitable for keratin materials:

(a) at least one amphiphilic polymer comprising at least one ethylenically unsaturated monomer containing a sulfonic group, in free form or partially or totally neutralized form, and also at least one hydrophobic portion, and (b) at least one oxidizing agent.

The invention also relates to the use of these polymers as thickeners and/or gelling agents in cosmetic and/or dermatological compositions comprising at least one oxidizing agent.

According to the invention, the oxidizing agent is preferably chosen from the group consisting of hydrogen peroxide and compounds capable of producing hydrogen peroxide by hydrolysis, or mixtures thereof.

However, other characteristics, aspects, subjects and advantages of the invention will emerge even more clearly on reading the description and the examples that follow.

AMPHIPHILIC POLYMERS ACCORDING TO THE INVENTION

The polymers in accordance with the invention are amphiphilic polymers comprising at least one ethylenically unsaturated monomer containing a sulfonic group, in free form or partially or totally neutralized form and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1000 to 20 000 000 g/mol, preferably ranging from 20 000 to 5 000 000 and even more preferably from 100 000 to 1 500 000 g/mol.

The amphiphilic polymers according to the invention may or may not be crosslinked. Crosslinked amphiphilic polymers are preferably chosen.

When they are crosslinked, the crosslinking agents may be chosen from polyolefinically unsaturated compounds commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyl-oxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulfonic group are chosen especially from vinylsulfonic acid, styrenesulfonic acid, (meth)acrylamido($C_1$-$C_{22}$)alkylsulfonic acids, and N—($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropane-sulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferably be used.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$-$C_{22}$ n-monoalkylamine or di-n-alkylamine, and such as those described in patent application WO-A-00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, patent U.S. Pat. No. 5,089,578 and in the following publications from Yotaro Morishima:

"Self-assembling amphiphilic polyelectrolytes and their nanostructures—Chinese Journal of Polymer Science Vol. 18,No. 40,(2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000,Vol. 33,No. 10-3694-3704";

"Solution properties of micelle networks formed by nonionic moieties covalently bound to a polyelectrolyte: salt effects on rheological behavior—Langmuir, 2000, Vol. 16,No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The ethylenically unsaturated hydrophobic monomers of these particular copolymers are preferably chosen from the acrylates or acrylamides of formula (I) below:

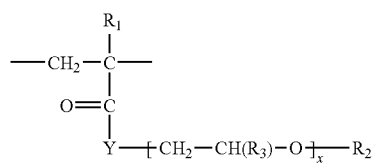
(I)

in which $R_1$ and $R_3$, which may be identical or different, denote a hydrogen atom or a linear or branched $C_1$-$C_6$ alkyl radical (preferably methyl); Y denotes O or NH; $R_2$ denotes a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x denotes a number of moles of alkylene oxide and ranges from 0 to 100.

The radical $R_2$ is preferably chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl radical.

According to one particularly preferred form of the invention, the monomer of formula (I) comprises at least one alkylene oxide unit ($x \geq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100,more preferably from 3 to 50 and even more preferably from 7 to 25.

Among these polymers, mention may be made of:

crosslinked or noncrosslinked, neutralized or nonneutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl (meth)acrylate units relative to the polymer, such as those described in patent application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in patent U.S. Pat. No. 5,089,578.

Mention may also be made of noncrosslinked and crosslinked copolymers of partially or totally neutralized AMPS and of dodecyl methacrylate, and also noncrosslinked and crosslinked copolymers of partially or totally neutralized AMPS and of n-dodecyl-methacrylamide, such as those described in the Morishima articles mentioned above.

Mention will be made more particularly of the copolymers consisting of 2-acrylamido-2-methylpropanesulfonic acid (AMPS) units of formula (II) below:

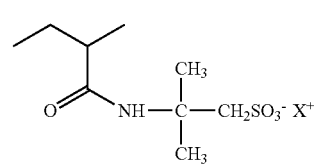
(II)

in which $X^+$ is a proton, an alkali metal cation, an alkaline-earth metal cation or the ammonium ion, and of units of formula (III) below:

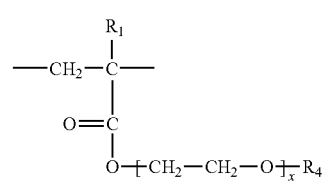
(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which x=25, $R_1$ denotes methyl and $R_4$ represents n-dodecyl; they are described in the Morishima articles mentioned above.

The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethylvaleronitrile, ABAH (2,2-azobis[2-amidinopropane]hydrochloride), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The amphiphilic polymers are obtained especially by free-radical polymerization in tert-butanol medium in which they precipitate.

Using precipitation polymerization in tert-butanol, it is possible to obtain a size distribution of the polymer particles that is particularly favorable for its uses.

The size distribution of the polymer particles may be determined, for example, by laser diffraction or image analysis.

An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen.

According to this process 2-acrylamido-2-methylpropanesulfonic acid (AMPS) or a sodium or ammonium salt thereof was especially polymerized with a (meth)acrylic acid ester and

- a $C_{10}$-$C_{18}$ alcohol oxyethylenated with 8 mol of ethylene oxide (Genapol® C-080 from the company Hoechst/Clariant),
- a $C_{11}$ oxo alcohol oxyethylenated with 8 mol of ethylene oxide (Genapol® UD-080 from the company Hoechst/Clariant),
- a $C_{11}$ oxo alcohol oxyethylenated with 7 mol of ethylene oxide (Genapol® UD-070 from the company Hoechst/Clariant),
- a $C_{12}$-$C_{14}$ alcohol oxyethylenated with 7 mol of ethylene oxide (Genapol® LA-070 from the company Hoechst/Clariant),
- a $C_{12}$-$C_{14}$ alcohol oxyethylenated with 9 mol of ethylene oxide (Genapol® LA-090 from the company Hoechst/Clariant),
- a $C_{12}$-$C_{14}$ alcohol oxyethylenated with 11 mol of ethylene oxide (Genapol® LA-110 from the company Hoechst/Clariant),
- a $C_{16}$-$C_{18}$ alcohol oxyethylenated with 8 mol of ethylene oxide (Genapol® T-080 from the company Hoechst/Clariant),
- a $C_{16}$-$C_{18}$ alcohol oxyethylenated with 15 mol of ethylene oxide (Genapol® T-150 from the company Hoechst/Clariant),
- a $C_{16}$-$C_{18}$ alcohol oxyethylenated with 11 mol of ethylene oxide (Genapol® T-110 from the company Hoechst/Clariant),
- a $C_{16}$-$C_{18}$ alcohol oxyethylenated with 20 mol of ethylene oxide (Genapol® T-200 from the company Hoechst/Clariant),
- a $C_{16}$-$C_{18}$ alcohol oxyethylenated with 25 mol of ethylene oxide (Genapol® T-250 from the company Hoechst/Clariant),
- a $C_{18}$-$C_{22}$ alcohol oxyethylenated with 25 mol of ethylene oxide and/or a $C_{16}$-$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol % and 99.9 mol %.

Preferably, for the most hydrophobic polymers, the molar proportion of units of formula (I) or (Ill) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The monomer distribution in the polymers of the invention may be, for example, alternating, block (including multi-block) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20 000 mPa.s to 100 000 mPa.s and more particularly from 60 000 mPa.s to 70 000 mPa.s.

The amphiphilic polymers in accordance with the invention are present in the compositions in concentrations ranging from 0.01% to 30% by weight of active material, more preferably from 0.1% to 10% of active material, even more preferably from 0.1% to 5% by weight of active material and even more particularly from 0.5% to 2% by weight.

Oxidizing Agent

The oxidizing agent for the composition according to the invention is preferably chosen from the group formed by aqueous hydrogen peroxide solution, urea peroxide and persalts such as perborates or persulfates, or mixtures thereof.

The oxidizing agent is preferably hydrogen peroxide, and even more preferably the oxidizing agent is aqueous hydrogen peroxide solution.

The hydrogen peroxide concentration can range from 0.5 to 40 volumes and preferably from 2 to 30 volumes, and that of the compound capable of forming hydrogen peroxide by hydrolysis can range from 0.1% to 25% by weight relative to the total weight of the oxidizing composition.

The oxidizing compositions according to the invention may be anhydrous or aqueous.

The oxidizing compositions according to the invention are preferably aqueous and the pH of the whole aqueous oxidizing composition preferably ranges from 1 to 13 and even more preferably from 2 to 12.

The oxidizing composition may also be, in particular in the case of bleaching, in the form of two parts to be mixed together at the time of use, one of these two parts containing alkaline agents and being in solid or liquid form. For hydrogen peroxide, the pH is preferably less than 7 before mixing.

The pH of the aqueous oxidizing compositions according to the invention may be obtained and/or adjusted conventionally by adding either basifying agents, for instance aqueous ammonia, monoethanolamine, diethanolamine, triethanolamine, isopropanolamine, 1,3-propanediamine, an alkali metal or ammonium carbonate or bicarbonate, an organic carbonate such as guanidine carbonate, or an alkali metal hydroxide, all these compounds obviously possibly being taken alone or as a mixture, or acidifying agents, for instance hydrochloric acid, acetic acid, lactic acid or boric acid.

The oxidizing composition may contain additives that are known for their use in oxidizing compositions for dyeing the hair by oxidation, or for permanently reshaping or bleaching the hair, such as acidifying or basifying agents, preserving agents, sequestering agents such as EDTA and etidronic acid, UV-screening agents, waxes, volatile or nonvolatile, cyclic or linear or branched silicones, which are organomodified (especially with amine groups) or not organomodified, ceramides, pseudoceramides, plant, mineral or synthetic oils, vitamins or provitamins, for instance panthenol, opacifiers, etc.

Preferably, when the oxidizing agent is aqueous hydrogen peroxide solution, the oxidizing composition according to the invention contains at least one stabilizer for the aqueous hydrogen peroxide solution. In compositions combining aqueous hydrogen peroxide solution and the amphiphilic polymers of the present invention, particularly advantageous results have been obtained by using at least one stabilizer chosen from alkali metal or alkaline-earth metal pyrophosphates, alkali metal or alkaline-earth metal stannates, phenacetin or salts of acids and of oxyquinoline, for instance oxyquinoline sulfate. Even more advantageously, at least one stannate optionally in combination with at least one pyrophosphate is used.

Salicylic acid and its salts, pyridinedicarboxylic acid and its salts, paracetamol and systems consisting of a) a buffer [an alkali metal (Na or K) or ammonium borate and preferably sodium tetraborate decahydrate], b) an alkaline agent ($NH_4OH$, monoethanolamine, ammonium carbonate, ammonium hydrogen carbonate or sodium hydroxide) and c) a sequestering agent for a heavy metal ion (Fe, Mn or Cu), such as those described in patent applications WO-01/72271, WO-01/72272 and WO-01/52801, may also be used.

In the oxidizing compositions according to the invention, the concentration of stabilizers for the aqueous hydrogen peroxide solution can range from 0.0001% to 5% by weight and preferably from 0.01% to 2% by weight relative to the total weight of the oxidizing compositions.

In the oxidizing compositions according to the invention containing aqueous hydrogen peroxide solution, the ratio of the concentrations of the hydrogen peroxide to the stabilizers can range from 0.05 to 1000,preferably from 0.1 to 500 and even more preferably from 1 to 200. Similarly, the ratio of the concentrations of the amphiphilic polymer(s) according to the invention to the stabilizers can range from 0.05 to 1000, preferably from 0.1 to 500 and even more preferably from 1 to 200.

In the oxidizing compositions according to the invention, the concentration of oxidizing agents ranges from 0.1% to 25% by weight relative to the total weight of the composition.

Preferably, according to the invention, the ratio of the concentrations of the amphiphilic polymer(s) according to the invention to the oxidizing agents is between 0.001 and 10,the amounts of said polymers and oxidizing agents being expressed as active materials (hydrogen peroxide for the aqueous hydrogen peroxide solution). Even more preferably, this ratio is between 0.01 and 5 and even more particularly between 0.02 and 1.

When the compositions according to the invention are generally in the form of a transparent gel, their viscosity preferably ranges from 50 mPa·s to 10 Pa·s and more preferably from 75 mPa·s to 0.5 Pa·s.

More particularly, the compositions according to the invention may also comprise at least one amphoteric or cationic substantive polymer.

Cationic Polymers

For the purposes of the present invention, the expression "cationic polymer" denotes any polymer containing cationic groups and/or groups which may be ionized into cationic groups.

The cationic polymers which may be used in accordance with the present invention may be chosen from any of those already known per se as improving the cosmetic properties of the hair, namely, in particular, those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5\times10^6$ approximately and preferably between $10^3$ and $3\times10^6$ approximately.

Among the cationic polymers which may be mentioned more particularly are polymers of the polyamine, polyamino amide and polyquaternary ammonium type.

These are known products. They are described in particular in French patents 2 505 348 and 2 542 997. Among said polymers, mention may be made of:

(1) homopolymers or copolymers derived from acrylic or methacrylic esters or amides and comprising at least one of the units of formula (I), (II), (III) or (IV) below:

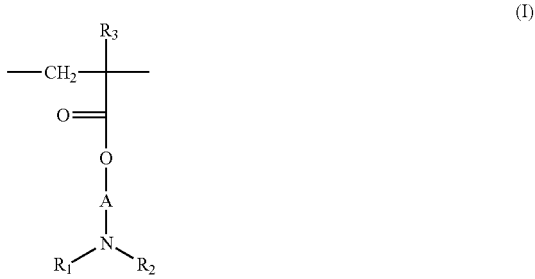

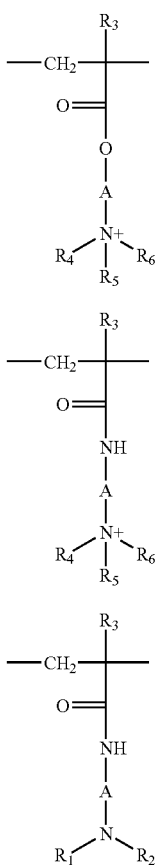

in which:
R$_3$, which may be identical or different, denote a hydrogen atom or a CH$_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl radical and preferably an alkyl group containing from 1 to 6 carbon atoms;
R$_1$ and R$_2$, which may be identical or different, represent hydrogen or an alkyl group containing from 1 to 6 carbon atoms, and preferably methyl or ethyl;
X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetoneacrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
the copolymers of acrylamide and of methacryloyloxyethyltrimethylammonium chloride described, for example, in patent application EP-A-080 976 and sold under the name Bina Quat P 100 by the company Ciba Geigy,
the copolymer of acrylamide and of methacryloyloxyethyltrimethylammonium methosulfate sold under the name Reten by the company Hercules,
quaternized or nonquaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers sold in particular under the name Styleze CC 10 by ISP, and
quaternized vinylpyrrolidone/dimethylaminopropylmethacrylamide copolymers such as the product sold under the name "Gafquat HS 100" by the company ISP.

(2) The cellulose ether derivatives containing quaternary ammonium groups, described in French patent 1 492 597, and in particular the polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloyloxyethyltrimethylammonium, methacrylamidopropyltrimethylammonium or dimethyldiallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

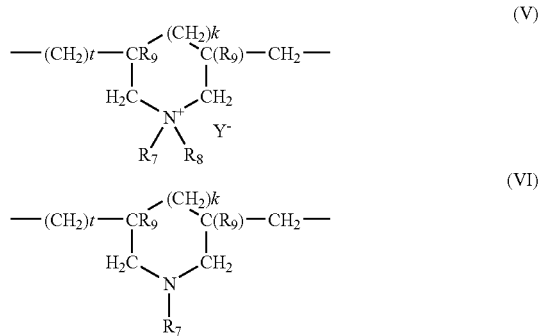

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 8 carbon atoms, a hydroxyalkyl group in which the alkyl group preferably has 1 to 5 carbon atoms, a lower $C_1$-$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; Y is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Calgon (and its homologs of low weight-average molecular mass) and copolymers of diallyidimethylammonium chloride and of acrylamide, sold under the name "Merquat 550".

(10) The quaternary diammonium polymer containing repeating units corresponding to the formula:

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and X⁻ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O—Z—O—, where Z denotes a linear or branched hydrocarbon-based radical or a group corresponding to one of the following formulae:

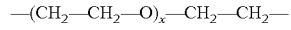

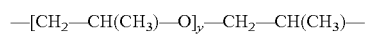

where x and y denote an integer from 1 to 4,representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

—CH$_2$—CH$_2$—S—S—CH$_2$—CH$_2$—;

d) a ureylene group of formula: —NH—CO—NH—.

Preferably, X$^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to formula (VIII) below:

$$-\underset{\underset{R_{11}}{|}}{\overset{\overset{R_{10}}{|}}{N^+}}-(CH_2)_n-\underset{\underset{R_{13}}{|}}{\overset{\overset{R_{12}}{|}}{N^+}}-(CH_2)_p- \quad X^- \quad X^- \quad \text{(VIII)}$$

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X$^-$ is an anion derived from a mineral or organic acid.

(11) Polyquaternary ammoniums consisting of repeating units of formula (IX):

$$\left[\underset{\underset{CH_3}{|}}{\overset{\overset{CH_3 \quad X^-}{|}}{N^+}}-(CH_2)_p-NH-CO-D-NH-(CH_2)_p-\underset{\underset{CH_3}{|}}{\overset{\overset{X^- \quad CH_3}{|}}{N^+}}-(CH_2)_2-O-(CH_2)_2\right] \quad \text{(IX)}$$

in which p denotes an integer ranging from 1 to 6 approximately, D may be nothing or may represent a group —(CH$_2$)$_r$—CO— in which r denotes a number equal to 4 or to 7,X$^-$ is an anion.

Such polymers may be prepared according to the processes described in U.S. Pat. Nos. 4,157,388, 4,702,906 and 4,719,282. They are described in particular in patent application EP-A-122 324.

Among these products, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as, for example, the products sold under the names Luviquat FC 905,FC 550 and FC 370 by the company BASF.

(13) Polyamines such as Polyquart H sold by Henkel, which are given under the reference name "Polyethylene glycol (15) tallow polyamine" in the CTFA dictionary.

(14) Crosslinked methacryloyloxy(C$_1$-C$_4$)alkyltri(C$_1$-C$_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (1), (9), (10), (11) and (14) and even more preferably the polymers consisting of repeating units of formulae (W) and (U) below:

$$-\left[\underset{\underset{CH_3}{|}}{\overset{\overset{CH_3}{|}}{N^+}}-(CH_2)_3-\underset{\underset{CH_3}{|}}{\overset{\overset{CH_3}{|}}{N^+}}-(CH_2)_6\right]- \quad \text{(W)}$$
$$\quad Cl^- \quad\quad Cl^-$$

and in particular those whose weight-average molar mass, determined by gel permeation chromatography, is between 9500 and 9900;

$$-\left[\underset{\underset{CH_3}{|}}{\overset{\overset{CH_3}{|}}{N^+}}-(CH_2)_3-\underset{\underset{C_2H_5}{|}}{\overset{\overset{C_2H_5}{|}}{N^+}}-(CH_2)_3\right]- \quad \text{(U)}$$
$$\quad Br^- \quad\quad Br^-$$

and in particular those whose weight-average molar mass, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers which may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers; K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537.

Mention may also be made of the sodium acrylate/acrylamidopropyltrimethyl-ammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) crosslinked and alkylated polyamino amides partially or totally derived from polyamino amides of general formula:

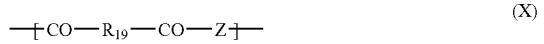

(X)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis (primary) or bis(secondary) amine, and Z denotes a bis(primary), mono- or bis(secondary)polyalkylene-polyamine radical and preferably represents:

a) in proportions of from 60 to 100 mol %, the radical

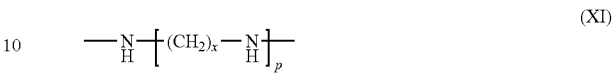

(XI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

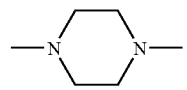

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) Polymers Containing Zwitterionic Units of Formula:

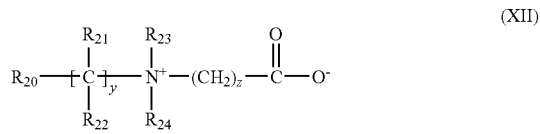

(XII)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethylcarboxymethylammonioethyl methacrylate such as the product sold under the name Diaformer Z301 by the company Sandoz.

(5) polymers derived from chitosan, described in particular in French patent No. 2 137 684 or U.S. Pat. No. 3,879,376, containing monomer units corresponding to formulae (XIII), (XIV) and (XV) below:

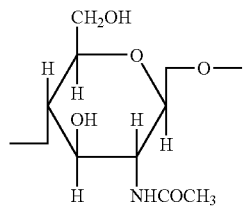

(XIII)

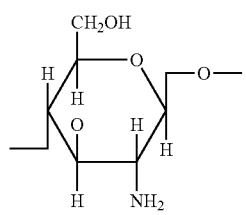

(XIV)

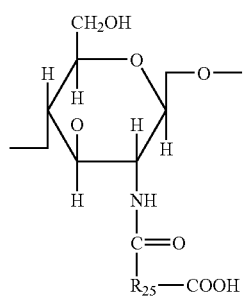

(XV)

the unit (XIII) being present in proportions of between 0 and 30%, the unit (XIV) in proportions of between 5% and 50% and the unit (XV) in proportions of between 30% and 90%, it being understood that, in this unit (XV), $R_{25}$ represents a radical of formula:

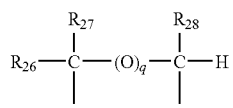

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, and also the salts formed by these compounds with bases or acids.

Polymers of this type that are more particularly preferred comprise from 0 to 20% by weight of units (XIII), from 40% to 50% by weight of units (XIV) and from 40% to 50% by weight of units (XV) in which $R_{25}$ denotes the radical —$CH_2$—$CH_2$—.

(6) polymers derived from the N-carboxyalkylation of chitosan, such as N-carboxymethylchitosan or N-carboxybutyl-chitosan sold under the name "Evalsan" by the company Jan Dekker.

(7) polymers corresponding to the general formula (XI) as described, for example, in French patent 1 400 366:

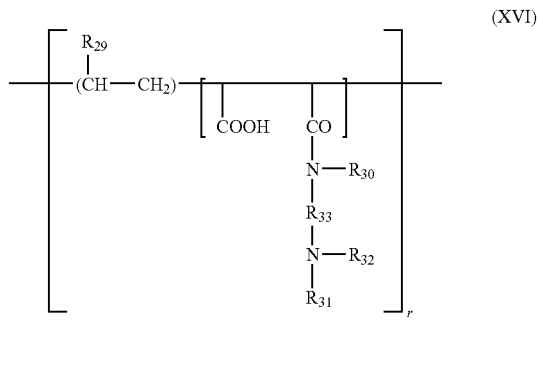

(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a —$CH_2$—$CH_2$—, —$CH_2$—$CH_2$—$CH_2$— or —$CH_2$—CH($CH_3$)— group, $R_{31}$ having the meanings mentioned above, and also the higher homologs of these radicals and containing up to 6 carbon atoms, r is such that the molecular weight is between 500 and 6 000 000 and preferably between 1000 and 1 000 000.

(8) amphoteric polymers of the type -D-X-D-X- chosen from:
a) polymers obtained by the action of chloroacetic acid or sodium chloroacetate on compounds containing at least one unit of formula:

-D-X-D-X-D- (XVII)

where D denotes a radical

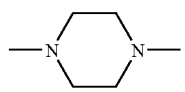

and X denotes the symbol E or E', E or E', which may be identical or different, denote a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

$$-D-X-D-X-\qquad\text{(XVIII)}$$

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) may represent from 0.01% to 10% by weight, preferably from 0.05% to 5% by weight and even more preferably from 0.1% to 3% by weight relative to the total weight of the composition.

The compositions of the invention preferably comprise one or more surfactants.

The surfactants may be chosen, without discrimination, alone or as mixtures, from anionic, amphoteric, nonionic, zwitterionic and cationic surfactants.

The surfactants that are suitable for carrying out the present invention are especially the following:

(i) Anionic Surfactant(s):

By way of example of anionic surfactants which can be used, alone or as mixtures, in the context of the present invention, mention may be made in particular (nonlimiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$alkyl sulfosuccinates, $(C_6-C_{24})$alkyl ether sulfosuccinates, $(C_6-C_{24})$alkylamide sulfosuccinates; $(C_6-C_{24})$alkyl sulfoacetates; $(C_6-C_{24})$acyl sarcosinates; and $(C_6-C_{24})$acyl glutamates. It is also possible to use $(C_6-C_{24})$alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991,pp. 116-178) and their nature is not a critical factor in the context of the present invention. Thus, they can be chosen in particular from (nonlimiting list) polyethoxylated or polypropoxylated, alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5,and in particular 1.5 to 4,glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides. It will be noted that alkylpolyglycosides are nonionic surfactants that are particularly suitable within the context of the present invention.

(iii) Amphoteric or Zwitterionic Surfactant(s):

The amphoteric or zwitterionic surfactants, the nature of which is not a critical factor in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982,under the names Amphocarboxyglycinates and Amphocarboxypropionates, with the respective structures:

$$R_2-CONHCH_2CH_2-N(R_3)(R_4)(CH_2COO^-)$$

in which: $R_2$ denotes an alkyl radical of an acid $R_2$—COOH present in hydrolyzed coconut oil, a heptyl, nonyl or undecyl radical, $R_3$ denotes a beta-hydroxyethyl group and $R_4$ denotes a carboxymethyl group; and $$R_2-CONHCH_2CH_2-N(B)(C)$$

in which:
B represents —$CH_2CH_2OX'$, C represents —$(CH_2)_z$—Y', with z=1 or 2, X' denotes the —$CH_2CH_2$—COOH group or a hydrogen atom, Y' denotes —COOH or the —$CH_2$—CHOH—$SO_3$H radical, $R_2$' denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993,under the names Disodium Cocoamphodiacetate, Disodium Lauroamphodiacetate, Disodium Caprylamphodiacetate, Disodium Capryloamphodiacetate, Disodium Cocoampho-dipropionate, Disodium Lauroamphopropionate, Disodium Caprylamphodipropionate, Disodium Caprylamphodipropionate, Lauroamphodipropionic acid and Cocoampho-dipropionic acid.

By way of example, mention may be made of the cocoamphodiacetate sold under the trade name Miranol® C2M concentrate by the company Rhodia Chimie.

(iv) Cationic Surfactants:

Among the cationic surfactants, mention may be made in particular (nonlimiting list) of: salts of optionally polyoxyalkylenated primary, secondary or tertiary fatty amines; quaternary ammonium salts such as tetraalkylammonium, alkylamidoalkyltrialkyl-ammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can range from 0.01% to 40% and preferably from 0.5% to 30% relative to the total weight of the composition.

The compositions according to the invention may also comprise other agents for adjusting the rheology, such as cellulose-based thickeners (hydroxyethylcellulose, hydroxypropylcellulose, carboxymethylcellulose, etc.), guar gum and its derivatives (hydroxypropylguar, etc.), gums of microbial origin (xanthan gum, scleroglucan gum, etc.), synthetic thickeners such as crosslinked acrylic acid or acrylamidopropanesulfonic acid homopolymers and nonionic, anionic, cationic or amphoteric associative polymers, such as the polymers sold under the names Pemulen TR1 or TR2 by the company Goodrich, Salcare SC90 by the company Allied Colloids, Aculyn 22, 28, 33, 44 or 46 by the company Rohm & Haas, and Elfacos T210 and T212 by the company Akzo.

These additional thickeners may represent from 0.01% to 10% by weight relative to the total weight of the composition.

Another subject of the invention is a process for the oxidation dyeing of human keratin fibers, and in particular the hair, using a dye composition comprising, in a support that is suitable for dyeing said fibers, at least one oxidation dye and an oxidizing composition as defined above.

According to this process, at least one dye composition as defined above is applied to the fibers, the color being developed at acidic, neutral or alkaline pH using an oxidizing composition according to the invention, which is applied simultaneously or sequentially, with or without intermediate rinsing.

According to one particularly preferred embodiment of the dyeing process according to the invention, the dye composition described above is mixed, at the time of use, with an oxidizing composition according to the invention. The mixture obtained is then applied to the keratin fibers and is left to act for 3 to 50 minutes approximately and preferably 5 to 30 minutes approximately, after which the fibers are rinsed, washed with shampoo, rinsed again and dried.

Another subject of the present invention is a process for permanently reshaping human keratin fibers and in particular the hair, using the composition defined above as oxidizing composition.

According to this process, a reducing composition is applied to the keratin fiber to be treated, the keratin fiber being placed under mechanical tension before, during or after said application, the fiber is optionally rinsed, the oxidizing composition of the present invention is applied to the optionally rinsed fiber, and the fiber is then optionally rinsed again.

The first step of this process consists in applying a reducing composition to the hair. This application is performed lock by lock or to the whole head of hair.

The reducing composition comprises at least one reducing agent, which may be chosen in particular from thioglycolic acid, cysteine, cysteamine, glyceryl thioglycolate, thiolactic acid, or thiolactic acid or thioglycolic acid salts.

The usual step for placing the hair under tension in a shape corresponding to the final shape desired for the hair (for example curls) may be performed by any means, especially any mechanical means, that is suitable and known per se for keeping the hair under tension, for instance rollers, curlers and the like.

The hair may also be shaped without the aid of external means, simply with the fingers.

Before performing the next optional rinsing step, it is conventionally appropriate to leave at rest for a few minutes, generally between 5 minutes and one hour and preferably between 10 and 30 minutes, the head of hair onto which the reducing composition has been applied, so as to allow the reducing agent sufficient time to act correctly on the hair. This waiting phase preferably takes place at a temperature ranging from 35° C. to 45° C., preferably while also protecting the hair with a hood.

In the second optional step of the process (step (ii)), the hair impregnated with the reducing composition is then thoroughly rinsed with an aqueous composition.

Next, in a third step (step (iii)), the oxidizing composition according to the present invention is applied to the hair thus rinsed, with the aim of fixing the new shape given to the hair.

As in the case of application of the reducing composition, the head of hair onto which the oxidizing composition has been applied is then, conventionally, left in a standing or waiting phase that lasts a few minutes, generally between 3 and 30 minutes and preferably between 5 and 15 minutes.

The vehicle for the reducing and oxidizing compositions used according to the invention is preferably an aqueous medium consisting of water and may advantageously contain cosmetically acceptable organic solvents including, more particularly, alcohols such as ethyl alcohol, isopropyl alcohol, benzyl alcohol and phenylethyl alcohol, or polyols or polyol ethers, for instance ethylene glycol monomethyl, monoethyl or monobutyl ether, propylene glycol or its ethers, for instance propylene glycol monomethyl ether, butylene glycol, dipropylene glycol, and also diethylene glycol alkyl ethers, for instance diethylene glycol monoethyl ether or monobutyl ether. The solvents may then be present in concentrations of between about 0.5% and 20% and preferably between about 2% and 10% by weight relative to the total weight of the composition.

If the hair was kept under tension by external means, these means (rollers, curlers and the like) may be removed from the hair before or after the fixing step.

Finally, in the last step of the process according to the invention (step (iv)), which is also an optional step, the hair impregnated with the oxidizing composition is rinsed thoroughly, generally with water.

A head of hair that is soft and easy to disentangle is finally obtained. The hair is wavy.

The oxidizing composition according to the invention may also be used in a process for bleaching human keratin fibers, and in particular the hair.

The bleaching process according to the invention comprises a step of applying an oxidizing composition according to the invention to the keratin fibers, this composition preferably comprising aqueous hydrogen peroxide solution in alkaline medium after extemporaneous, mixing. Conventionally, a second step of the bleaching process according to the invention is a step of rinsing the keratin fibers.

The examples that follow illustrate the invention without being limiting in nature.

PREPARATION EXAMPLES

Preparation of Ethoxylated (Meth)Acrylic Esters

These may especially be obtained by the action of glycidyl (meth)acrylate or (meth)acrylic acid or an alkyl(meth)acrylate or a (meth)acryloyl halide on an ethoxylated fatty alcohol. Nonlimiting examples that may be mentioned include the following preparations:

a) starting with glycidyl methacrylate and Genapol T-250;
    b) starting with (meth)acrylic acid and Genapol UD-070;
    c) starting with methyl(meth)acrylate and Genapol LA-090;
    d) starting with (meth)acryloyl chloride and Genapol UD-070.

a) 500 g of Genapol T-250 and 75 g of glycidyl methacrylate are placed in a one-liter three-necked reactor equipped with a stirrer, a thermometer and a reflux condenser. The reaction mixture is heated at a temperature of 100° C. for 2 hours and the excess glycidyl methacrylate is removed by distillation under reduced pressure. The monomer obtained may be used for the polymerization without further purification.

b) 500 g of Genapol UD-070, 100 g of (meth)acrylic acid and p-toluenesulfonic acid as catalyst are placed in a one-liter three-necked reactor equipped with a stirrer, a thermometer and a reflux condenser. The reaction mixture is refluxed for 2 hours and the excess acid and the water formed during the reaction are separated out by distillation under reduced pressure. The monomer obtained may be used for the polymerization without further purification.

c) 500 g of Genapol LA-090, 100 g of methyl(meth)acrylate and 20 g of titanium tetraisopropoxide are placed in a one-liter three-necked reactor equipped with a stirrer, a thermometer and a reflux condenser. The reaction mixture is refluxed for 2 hours and, after separation by distilling off the alcohol formed, the remaining ester is distilled under reduced pressure. The monomer obtained may be used for the polymerization without further purification.

d) 500 g of Genapol UD-070, 110 g of (meth)acryloyl chloride and 50 g of sodium carbonate are placed in a one-liter three-necked reactor equipped with a stirrer, a thermometer and a reflux condenser. The reaction mixture is refluxed for 2 hours and the excess acid chloride is separated out by distillation under reduced pressure. The monomer obtained may be used for the polymerization without further purification.

Polymerization According to the Precipitation Method in Tert-butanol 500 ml of tert-butanol and the calculated amount of AMPS are placed in a 2-liter reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon through, and, when the internal temperature has reached 60° C., the initiator (AIBN) is introduced to initiate the polymerization.

After a few minutes, the polymer thus prepared precipitates. The mixture is maintained at reflux for 2 hours, and the polymer is separated from the solvent by vacuum filtration and then dried under reduced pressure.

The following polymers were prepared in the manner described above: (starting with the following reagents in amounts expressed in grams)

| | | | | |
|---|---|---|---|---|
| Genapol T-250 methacrylate . . . | 10 | 20 | 30 | 97 |
| AMPS neutralized with $NH_3$ . . . | 90 | 80 | 90 | 3 |
| Methylenebisacrylamide (crosslinking agent) . . . | | | 1.5 | |
| Allyl methacrylate (crosslinking agent) . . . | | 1.7 | | |
| TMPTA (crosslinking agent) . . . | 1.8 | | | 1.8 |
| Azobisisobutyronitrile (initiator) . . . | | | 1 | |
| Dilauryl peroxide (initiator) . . . | 1 | 1 | | 1 |
| tert-Butanol . . . | 300 | 300 | 300 | 300 |

Example 1

Oxidation Dye Composition

Dye Composition:

The dark chestnut-brown shade from the commercial range Excellence Creme® from L'Oréal was used.

Oxidizing Composition

| | |
|---|---|
| Acrylamido-2-methyl-2-propanesulfonic acid/n-dodecylacrylamide copolymer (3.5%/96.5%) 100% neutralized with sodium hydroxide . . . | 1 g |
| Hydrogen peroxide . . . qs . . . | 20 volumes |
| Tetrasodium pyrophosphate (0.02 g) and sodium stannate (0.04 g) | |
| Sequestering agent: pentasodium pentaacetate . . . | 0.06 g AM* |
| Demineralized water . . . qs . . . | 100 g |

AM* denotes Active Material

At the time of use, the dye composition was mixed with the oxidizing composition in a 1/1.5 weight ratio.

The mixture obtained was applied to locks of gray hair containing 90% white hairs, at a rate of 10 g per 1 g of hair, and left to act for 30 minutes.

The hair was then rinsed, washed with a standard shampoo and then dried.

A uniform dark chestnut-brown shade was obtained.

Example 2

Permanent-reshaping Composition

The reducing composition below (expressed in grams) was prepared:

| | |
|---|---|
| Thioglycolic acid . . . | 9.2 |
| Arginine . . . | 15 |
| Aqueous ammonia containing 20% $NH_3$ . . . | 9.3 |
| Ammonium carbonate . . . | 4.5 |
| Cocoylamidopropylbetaine/glyceryl monolaurate (25/5) as an | 1.3 |

| -continued | |
|---|---|
| aqueous 30% solution ... | |
| Peptizer ... | 0.8 |
| Isostearyl alcohol (Tego Alkanol 66 sold by the company Goldschmidt) ... | 12 |
| Sequestering agent ... | 0.4 |
| Fragrance ... | 0.4 |
| Demineralized water ... qs ... | 100 |

This reducing composition was applied to a lock of wet hair rolled up beforehand on a curler 9 mm in diameter.

After an action time of 10 minutes, the lock was rinsed thoroughly with water.

The oxidizing composition below was then applied.

Oxidizing Composition:

| | |
|---|---|
| Acrylamido-2-methyl-2-propanesulfonic acid/ n-dodecylacrylamide copolymer (3.5%/96.5%) 100% neutralized with sodium hydroxide ... | 1 g |
| Aqueous hydrogen peroxide solution ... | 8 volumes |
| Tetrasodium pyrophosphate (0.02 g) and sodium stannate (0.04 g) | |
| Sequestering agent: pentasodium pentaacetate ... | 0.06 g AM* |
| Demineralized water ... qs ... | 100 g |

AM* denotes Active Material

After an action time of 10 minutes, the lock was again rinsed thoroughly with water.

The hair was then unwound from the curler and dried.

The lock was wavy.

Similar results were obtained by replacing the acrylamido-2-methyl-2-propanesulfonic acid/n-dodecylacrylamide copolymer neutralized with sodium hydroxide, of the above Examples 1 and 2, with a copolymer crosslinked with methylenebisacrylamide consisting of 75% by weight of AMPS units neutralized with $NH_3$ and 25% by weight of units of formula (III) in which $R_1$=H, $R_4$=$C_{16}$-$C_{18}$ and x=25.

Similar results were obtained by replacing the acrylamido-2-methyl-2-propanesulfonic acid/n-dodecylacrylamide copolymer neutralized with sodium hydroxide, of the above Examples 1 and 2, with a copolymer crosslinked with allyl methacrylate consisting of 90% by weight of AMPS units neutralized with $NH_3$ and 10% by weight of Genapol T-250 methacrylate units [units of formula (III) in which $R_1$=$CH_3$, $R_4$=$C_{16}$-$C_{18}$ and x=25], or with a copolymer crosslinked with allyl methacrylate consisting of 80% by weight of AMPS units neutralized with $NH_3$ and 20% by weight of Genapol T-250 methacrylate units [units of formula (III) in which $R_1$=$CH_3$, $R_4$=$C_{16}$-$C_{18}$ and x=25].

The invention claimed is:

1. A cosmetic and/or dermatological composition for treating keratin materials, which comprises:
    (a) at least one amphiphilic polymer comprising:
        at least one 2-acrylamido-2-methylpropanesulfonic acid (AMPS) unit of formula (II) below:

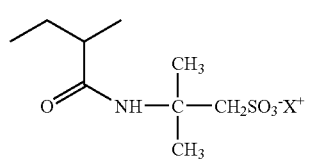

(II)

in which $X^+$ is selected from the group consisting of proton, an alkali metal cation, an alkaline-earth metal cation, and an ammonium ion; and
    at least one unit of formula (III) below:

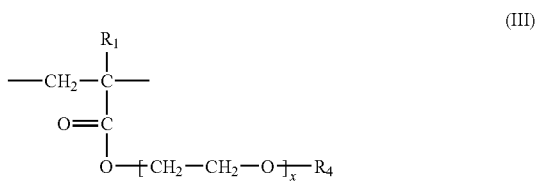

(III)

in which x is wherein the amphiphilic polymer is present in concentrations ranging from 0.01% to 30% by weight, relative to the total weight of the composition 25, $R_1$ is a methyl group, and $R_4$ is an $C_{12}$ to $C_{18}$ alkyl radical; and
    (b) at least one oxidizing agent;
    wherein the amphiphilic polymer is crosslinked.

2. The composition as claimed in claim 1, wherein the amphiphilic polymer is partially or totally neutralized with a mineral or organic base.

3. The composition as claimed in claim 1, wherein the amphiphilic polymer has a number-average molecular weight ranging from 1000 to 20 000 000 g/mol.

4. The composition as claimed in claim 3, wherein the number-average molecular weight ranges from 20 000 to 5 000 000 g/mol.

5. The composition as claimed in claim 4, wherein the number-average molecular weight ranges from 100 000 to 1 500 000 g/mol.

6. The composition as claimed in claim 1, wherein an aqueous solution at 1% by weight of the amphiphilic polymer has, at a temperature of 25° C., a viscosity, measured using a Brookfield viscometer with a No. 7 needle, ranging from 20 000 mPa.s to 100 000 mPa.s.

7. The composition as claimed in claim 1, wherein the amphiphilic polymer is prepared by free-radical precipitation polymerization in tert-butanol.

8. The composition as claimed in claim 1, wherein the amphiphilic polymer is crosslinked using a polyolefinically unsaturated compound.

9. The composition as claimed in claim 8, wherein the polyolefinically unsaturated compound is selected from the group consisting of methylenebisacrylamide, allyl methacrylate and trimethylolpropane triacrylate (TMPTA).

10. The composition as claimed in claim 1, wherein a degree of crosslinking of the amphiphilic polymer ranges from 0.01 mol % to 10 mol % relative to the polymer.

11. The composition as claimed in claim 1, wherein the oxidizing agent comprises at least one member selected from the group consisting of hydrogen peroxide, urea peroxide, perborates and persulfates.

12. The composition as claimed in claim 1, wherein the oxidizing agent comprises hydrogen peroxide.

13. The composition as claimed in claim 12, wherein the oxidizing agent comprises an aqueous hydrogen peroxide solution.

14. The composition as claimed in claim 13, wherein the aqueous hydrogen peroxide solution comprises a stabilizer.

15. The composition as claimed in claim 14, wherein the stabilizer is selected from the group consisting of alkali metal pyrophosphates, alkaline-earth metal pyrophosphates, alkali metal stannates; alkaline-earth metal stannates, phenacetin, salts of acids and salts of oxyquinoline.

16. The composition as claimed in claim 15, wherein the stabilizer comprises a stannate or a stannate combined with a pyrophosphate.

17. The composition as claimed in claim 14, wherein the stabilizer is present in an amount of from 0.0001% to 5% by weight relative to the total weight of the composition.

18. The composition as claimed in claim 14, wherein a ratio of a concentration of the hydrogen peroxide to a concentration of the stabilizer ranges from 0.05 to 1000.

19. The composition as claimed in claim 14, wherein a ratio of a concentrations of the amphiphilic polymer to a concentration of the stabilizer ranges from 0.05 to 1000.

20. The composition as claimed in claim 1, wherein a ratio of a concentrations of the amphiphilic polymer to a concentration of the oxidizing agent ranges from 0.001 to 10.

21. The composition as claimed in claim 11, wherein the oxidizing agent is present in a concentration of from 0.1% to 25% by weight relative to the total weight of the composition.

22. The composition as claimed in claim 1, wherein the composition is aqueous and a pH of the composition ranges from 1 to 13.

23. The composition as claimed in claim 1, wherein the composition is in the form of a transparent gel with a viscosity ranging from 50 mPa.s to 10 Pa.s.

24. A kit for the oxidation dyeing of human keratin fibers hair, which comprises at least one oxidation dye and the composition as defined in claim 1.

25. The composition as claimed in claim 1, wherein the amphiphilic polymer is present in an amount ranging from 0.1 to 10% by weight relative to the total weight of the composition.

26. The composition as claimed in claim 1, wherein the amphiphilic polymer is present in an amount ranging from 0.1% to 5% by weight relative to the total weight of the composition.

27. The composition as claimed in claim 1, wherein the amphiphilic polymer is present in an amount ranging from 0.5% to 2% by weight relative to the total weight of the composition.

28. The composition as claimed in claim 14, wherein the stabilizer is present in an amount of from 0.01% to 2% by weight relative to the total weight of the composition.

29. The composition as claimed in claim 14, wherein a ratio of a concentrations of the hydrogen peroxide to a concentration of the stabilizer ranges from 0.1 to 500.

30. The composition as claimed in claim 14, wherein a ratio of a concentrations of the hydrogen peroxide to a concentration of the stabilizer ranges from 1 to 200.

31. The composition as claimed in claim 14, wherein a ratio of a concentrations of the amphiphilic polymer to a concentration of the stabilizer ranges from 0.1 to 500.

32. The composition as claimed in claim 12, wherein a ratio of a concentrations of the amphiphilic polymer to a concentration of the stabilizer ranges from 1 to 200.

33. The composition as claimed in claim 1, wherein a ratio of a concentrations of the amphiphilic polymer to a concentration the oxidizing agent ranges from 0.01 to 5.

34. The composition as claimed in claim 1, wherein a ratio of a concentrations of the amphiphilic polymer to a concentration of the oxidizing agent ranges from 0.02 to 1.

35. The composition as claimed in claim 1, wherein the composition is aqueous and a pH of the composition ranges from 2 to 12.

36. The composition as claimed in claim 1, wherein the composition is in the form of a transparent gel with a viscosity ranging from 75 mPa.s to 0.5 Pa.s.

37. A process for the oxidation dyeing of human hair that comprises:
mixing the kit components as claimed in claim 24;
contacting the mixed kit components to human hair for a period of about 3 to 50 minutes;
rinsing the human hair;
washing the human hair with shampoo; followed by
rinsing the human hair; and
drying the human hair.

38. A process for the oxidation dyeing of human hair that comprises:
mixing the kit components as claimed in claim 24;
contacting the mixed kit components to human hair for a period of about 5 to 30 minutes;
rinsing the human hair;
washing the human hair with shampoo; followed by
rinsing the human hair; and
drying the human hair.

39. A process for permanently reshaping human hair, which comprises:
applying a reducing composition to the human hair; wherein mechanical tension is applied to the human hair before, during or after the applying step;
optionally rinsing the human hair;
applying the composition of claim 1 to the optionally rinsed human hair; and
optionally rinsing the human hair.

40. A process for permanently forming waved human hair, which comprises:
applying a reducing composition to the human hair; wherein mechanical tension is applied to the human hair before, during or after the applying step;
optionally rinsing the human hair;
applying the composition of claim 1 to the optionally rinsed human hair; and
optionally rinsing the human hair.

41. A process for bleaching human hair, which comprises:
applying the composition of claim 1 to human hair; and
rinsing the human hair.

\* \* \* \* \*

UNITED STATES PATENT AND TRADEMARK OFFICE
CERTIFICATE OF CORRECTION

PATENT NO. : 7,862,803 B2
APPLICATION NO. : 10/451409
DATED : January 4, 2011
INVENTOR(S) : Sylvain Kravtchenko et al.

It is certified that error appears in the above-identified patent and that said Letters Patent is hereby corrected as shown below:

Column 28, lines 15-17, "in which x is wherein the amphiphilic polymer is present in concentrations ranging from 0.01% to 30% by weight, relative to the total weight of the composition 25," should read --in which x is 25,--; thus, please delete "wherein the amphiphilic polymer is present in concentrations ranging from 0.01% to 30%) by weight, relative to the total weight of the composition".

line 20, "crosslinked" should read --crosslinked, wherein the amphiphilic polymer is present in concentrations ranging from 0.01% to 30% by weight, relative to the total weight of the composition."; thus, after crosslinked, please insert --wherein the amphiphilic polymer is present in concentrations ranging from 0.01% to 30% by weight, relative to the total weight of the composition.--.

Column 29, lines 25-26, "dyeing of human keratin fibers hair" should read "dyeing of human hair"; thus please delete "keratin fibers".

Signed and Sealed this
Twenty-third Day of August, 2011

David J. Kappos
*Director of the United States Patent and Trademark Office*